United States Patent [19]

Kamentsky et al.

[11] Patent Number: 5,107,422
[45] Date of Patent: Apr. 21, 1992

[54] METHOD AND APPARATUS FOR MEASURING MULTIPLE OPTICAL PROPERTIES OF BIOLOGICAL SPECIMENS

[76] Inventors: Louis A. Kamentsky, 180 Beacon St., #17G, Boston, Mass. 02116; Lee D. Kamentsky, 79 Paul Gore St., Jamaca Plain, Mass. 02130

[21] Appl. No.: 583,075

[22] Filed: Sep. 14, 1990

Related U.S. Application Data

[63] Continuation-in-part of Ser. No. 416,031, Oct. 2, 1989, Pat. No. 5,072,382.

[51] Int. Cl.$^5$ .............................................. G06K 9/00
[52] U.S. Cl. .................................... 364/413.08; 382/6
[58] Field of Search ........................ 250/359.1, 360.1; 364/506, 556, 525, 413.1, 413.8, 413.07, 555, 497, 413.13; 356/408, 432; 358/106, 107, 903; 382/50, 52, 6

[56] References Cited

U.S. PATENT DOCUMENTS

| | | | |
|---|---|---|---|
| 3,918,812 | 11/1975 | Holm | 356/73 |
| 3,999,047 | 12/1976 | Green | 382/6 |
| 4,045,772 | 8/1977 | Bouton et al. | 382/6 X |
| 4,060,713 | 11/1977 | Goulay | 382/6 X |
| 4,097,845 | 6/1978 | Bacus | 358/107 X |
| 4,122,518 | 10/1978 | Castleman et al. | 364/900 X |
| 4,125,828 | 11/1978 | Resnick et al. | 364/413.08 X |
| 4,129,854 | 12/1978 | Suzuki et al. | 364/413.08 X |
| 4,175,859 | 11/1979 | Hashizume et al. | 364/413.08 X |
| 4,199,748 | 4/1980 | Bacus | 382/6 |
| 4,229,797 | 10/1980 | Ledley | 382/6 X |
| 4,284,412 | 8/1981 | Hansen et al. | 436/808 |
| 4,513,438 | 4/1985 | Graham et al. | 382/6 |
| 4,523,278 | 6/1985 | Reinhardt et al. | 364/413.1 |
| 4,612,614 | 9/1986 | Deindoerfer et al. | 364/413.02 |
| 4,636,456 | 1/1987 | Elials et al. | 364/578 |
| 4,647,531 | 5/1987 | Kamentsky | 435/7.24 |
| 4,665,553 | 5/1987 | Gershman et al. | 382/6 |
| 4,672,559 | 6/1987 | Jansson et al. | 382/6 X |
| 4,695,884 | 9/1987 | Anastassion et al. | 382/51 X |
| 4,700,298 | 10/1987 | Palaic et al. | 364/413.1 X |
| 4,741,043 | 4/1988 | Bacus | 358/107 X |
| 4,794,531 | 12/1988 | Morishita et al. | 364/413.13 |
| 4,833,723 | 5/1989 | Leveridge et al. | 382/53 |
| 4,977,605 | 12/1990 | Fardeau et al. | 382/53 X |
| 5,016,173 | 5/1991 | Kenet et al. | 364/413.13 |

FOREIGN PATENT DOCUMENTS

2508523 of 0000 Fed. Rep. of Germany.

OTHER PUBLICATIONS

Megla, G. K., *The LARC Automatic White Blood Cell Analyzers*, Acta Cytologica, vol. 17(1):3-14 (1973).
Green, J. E., *A Practical Application of Computer Pattern Recognition Research: The Abbott ADC-500 Differential Classifier*, J. Histochem. and Cytochem., vol. 27(1):160-173 (1979).
Shack, R. et al., *Ultrafast Laser Scanner Microscope*, J. Histochem. Cytochem., 27(1):153-159 (1979).

(List continued on next page.)

*Primary Examiner*—Parshotam S. Lall
*Assistant Examiner*—S. A. Melnick
*Attorney, Agent, or Firm*—Fish & Richardson

[57] ABSTRACT

The invention relates to an apparatus and methods for generating multiparameter optical data that characterize a population of cells. The invention includes the steps of scanning the cell population with a beam to produce sets of digital data samples, each sample set of digital data representing multiparameter optical interactions from a specific location within the cell population; storing the digital data, e.g., in a computer memory; locating a cell within the population, e.g., by comparing the digital data to a preselected threshold value; defining a neighborhood around the digital data representing the located cell; estimating a background level for the neighborhood based upon digital data corresponding to locations outside the neighborhood; and correcting each of the samples corresponding to the neighborhood with the estimated neighborhood background level to generate the optical data. The invention further relates to specific methods of background correction and data calibration as well as specific sampling features to enable precise estimates of multiple cellular constituents or other cell properties at high rates of speed.

13 Claims, 9 Drawing Sheets

OTHER PUBLICATIONS

Reich, S., *Precision Digital Position Encoding for Resonant Scanners*, SPIE Laser Scanning Recording, vol. 498:169-174 (1984).

Reich, S., *The Use of Electro–Mechanical Mirror Scanning Devices*, SPIE Laser Scanning Components & Techniques, vol. 84:47-56 (1976).

Tweed, D. G., *Resonant Scanner Linearization Techniques*, SPIE Laser Scanning and Recording, vol. 498:161-168 (1984).

Martin, J. C., *Time: A New Parameter for Kinetic Measurements in Flow Cytometry*, Science, vol. 207:199-201 (1980).

Bartels, P. H. et al., *Computer Analysis Biomedical Interpretation of Microscopic Images: Current Problems and Future Directions*, Proceedings of the IEEE, vol. 65 (2):252-261 (1977).

Carlsson, K. et al., *Confocal Imaging for 3-D Digital Microscopy*, Applied Optics, vol. 26(16):3232-38 (1987).

Burger, D. et al., *Acousto-Optic Laser-Scanning Cytometer*, Cytometry, vol. 9:101-110 (1988).

Kamentsky, L. A., *Cell Identification and Sorting*, Chapter 4, Computers in Biochemical Research, 3 (1969) (107-144).

Kamentsky, L. A., *Future Directions for Flow Cytometry*, J. Histochem. Cytochem., vol. 27(12):1649-51 (1979).

Shoemaker, R. L. et al., *An Ultrafast Laser Scanner Microscope for Digital Image Analysis*, IEEE Transactions on Biomedical Engineering, vol. BME-29 (2):82-91 (1982).

Van Driel-Kulker, A. M. J., et al., *The Use of LEYTAS in Analytical and Quantitative Cytology*, IEEE Transactions on Biomedical Engineering, vol. BME-29(2):92-100 (1982).

Mellors, R. C. et al., *Microfluorometric Scanner for the Differential Detection of Cells: Application to Exfoliative Cytology*, Science, vol. 114:356-360 (1951).

Sawyer, H. S. et al., *A New Nipkon-Disk Scanner for Accurate Cytological Measurements*, I.R.E. National Convention Record, Part 9:37-42 (1958).

McCarthy, B. D., *Automatic Determination of Morphological Parameters in Biological Materials by a Flying Spot Microscope*, Cytology Automation: Proceedings of Second Tenovus Symposium (1968) (231-242).

Lovett, E. J. et al., *Application of Flow Cytometry to Diagnostic Pathology*, Laboratory Investigation, vol. 50(2):115-139 (1984).

Cambridge Instruments, Quantimet 520, Image Analysis System (1986).

Cell Analysis System, CAS 100 System (1985).

Perceptics Corporation, BioVision (1987).

Meridian Instruments, Inc., ACAS 470 (1986).

Tracor Northern, TSM.

Becton Dickinson, FACScan (1986).

Coulter Corporation, PROFILE.

"An Introduction to Data Analysis", Chapter 5, *Practical Flow Cytometry*, second edition, Alan R. Liss, Inc., Dec. 1985.

"Cytometric Data Processing", Chapter 20, *Flow Cytometry and Sorting*, John Wiley & Sons, Dec. 1979.

METHOD AND APPARATUS FOR MEASURING MULTIPLE OPTICAL PROPERTIES OF BIOLOGICAL SPECIMENS

BACKGROUND OF THE INVENTION

This is a continuation-in-part of U.S. Ser. No. 416,031 filed on Oct. 2, 1989, now U.S. Pat. No. 5,072,382.

This invention relates to measuring multiple optical properties of biological specimens, such as a population of cells, e.g., blood cells, at high rates of speed using computer controlled instruments that scan the biological specimens.

Examples of such computer controlled instruments include flow cytometers, automated blood cell analyzers and blood cell differential classifiers.

A flow cytometer is an instrument that hydrodynamically focuses a fluid suspension of cells into a single file stream that passes through an examination zone. A focused light beam illuminates the cells in this zone and the instrument measures optical interactions of the light with the cells such as, for example, multiple wavelength absorption, scatter as a function of angle, and fluorescence as a function of either wavelength or polarization. This type of instrument permits the study of living cells in addition to those which have been chemically treated, for example, by staining. Flow cytometry techniques enable certain constituents or structures, particularly those present on the cell surface, to be quantitatively characterized at cell rates of a thousand or more cells per second.

Blood cell analyzers typically consist of a computerized microscope that automatically classifies various types of white blood cells and flags and counts all abnormal cells in a specimen. Using such an automated instrument, the operator can also view the cells manually, stop the analyzer temporarily for making visual morphological observations, or review abnormal cells in greater detail. During the automatic count, the X-Y coordinates of every encountered abnormal blood cell are stored. Therefore, the operator has the option of using a review mode in which abnormal cells are automatically and individually acquired and focused, and can view these cells on a T.V. monitor or through a binocular microscope.

A blood cell differential classifier typically consists of a computer-controlled microscope having a stage that is driven by stepper motors. A light source, such as a xenon arc lamp, illuminates cells and the classifier uses various sensors such as a silicon photodiode array to measure the optical interaction between the cells and the light. All of the cells in a given area are illuminated at the same time.

SUMMARY OF THE INVENTION

In general, the invention features a method and apparatus for generating optical data that accurately estimates multiple constituents and simultaneously characterizes a number of morphological properties of each of a population of cells. This method includes the steps of, and means for scanning the cell population with a beam to produce digital data samples, the different digital data samples representing multiple optical measurements at different locations within the cell population; storing the digital data, e.g., in a computer memory; locating a cell within the population, for example by comparing digital data derived from the stored digital data to a preselected threshold value; defining a neighborhood around the located cell; estimating a background level or individual background levels for all sample points in the neighborhood based upon stored digital data corresponding to locations outside the neighborhood; and correcting each of the digital data samples corresponding to the neighborhood with the estimated neighborhood background level to generate the optical data. The beam used in the invention is of electromagnetic radiation, e.g., laser light, X-rays, or infrared radiation.

The sample correcting step may be performed by subtracting the corresponding background level from each of the stored digital data samples in a neighborhood.

The term "digital data sample" describes digital information that may be stored in a computer memory and that is sampled from an analog optical signal from the population of cells in a specimen when scanned with the beam. The optical data results from correction of the digital data for background. Further processing of the optical data generates corresponding optical and morphological property values of the population of cells that may be used for precise measurements of cellular constituents and as representations of cellular morphology.

The term "constituent" as used herein refers to a specific part or component of a cell such as, for example, the DNA or RNA. The invention is capable of determining the amount of a specific constituent in a cell or cell population with an accuracy of within about a few percent of the actual amount.

The term "neighborhood" means a specific region of sample points that is created by the operator to encompass the digital data and that is set to statistically correspond to a single cell. That is, on average, only one cell will be located within a neighborhood. The size of such a neighborhood may be varied by the operator depending upon the size and concentration of the cells in the specimen. The neighborhood is used to allow an accurate estimate of cell constituents by determining the background within each neighborhood, i.e., individually for each cell. This allows for greater accuracy than a background level used for a number of different cells, because the background level varies across the examining surface, such as a microscope slide.

The invention also features a method and apparatus for generating optical data that characterizes a population of cells that includes the steps of, and means for, scanning the cell population with a beam with a spot size comparable in size to the cells to be scanned to produce digital data samples, in which different samples represent different locations within the cell population and the rate of sampling is such that the distance traveled per time as the spot is scanned between consecutive sampled locations approximates the spot size; and then processing the digital data to generate optical data that characterizes the cells in the population. The term "comparable" as used herein means within one order of magnitude of the size of the cells to be scanned.

In general, the number of sample points required to represent a cell is equal to the number of samples taken along a scan times the number of scans. When a small spot size of, e.g., one-half micron is used, as in the prior art, on the order of four hundred samples are required to accurately represent the constituents in a 10 micron by 10 micron cell area. According to the present invention, the spot size is on the order of 10 microns in diameter and is sampled at a rate such that the distance traveled per time as the spot is scanned between consecutive sampled locations is approximately the spot size. This gives the benefit of processing a sample about four hundred times faster than with the small spot size without losing accuracy. As the size is decreased and the sampling rate is increased this benefit correspondingly decreases.

This method may also include the steps of multiplying the neighborhood value by a velocity normalization factor proportional to the velocity at which the beam is scanned past each location to generate optical data calibrated for scanning velocity variations.

In another aspect, the invention features a method and apparatus for generating calibrated optical data that characterizes a population of cells including the steps of, and means for, measuring the resulting intensity of a beam having a predetermined incident illumination intensity used to scan the cell population as a function of location of each sample within the scan; scanning the cell population with the beam to produce digital data samples, different samples representing different locations within the cell population; storing the digital data, e.g., in memory; normalizing the stored digital data using the beam intensity measurements of the location of each sample within the scan; and then processing the normalized digital data to generate calibrated optical data that characterizes the cells in the population. The resulting beam intensity may be measured, for example, with a sensor, such as a photomultiplier.

The invention also features a method and apparatus for generating calibrated optical data that characterizes a population of cells, that includes the steps of and means for, scanning the cell population on a surface with a beam to produce digital data samples, the beam having a given illumination intensity, and different samples representing different locations within the cell population; storing the digital data, e.g., in a memory; scanning a region of the surface without cells to generate intensity calibration data; generating an intensity normalization factor from the intensity calibration data and storing the intensity normalization factor in memory; locating a cell within the population, e.g., by comparing the digital data to a preselected threshold; defining a neighborhood around the located cell, the neighborhood containing optical data derived from the samples of digital data within the neighborhood; and correcting the optical data in a neighborhood, e.g., by multiplying the optical data by the intensity normalization factor, to generate the calibrated optical data.

The surface without cells may be a calibration slide including a uniform fluorescent dye surface, a dye-filled cuvette or a uniform scattering surface.

In another embodiment, the processing step may include multiplying the digital data by a velocity normalization factor proportional to the velocity at which the light beam is scanned by each location to generate optical data calibrated for scanning velocity variations.

The method may also include the further steps of estimating background levels for the individual neighborhoods based upon stored digital data corresponding to each optical parameter at locations outside that neighborhood; and correcting each of the digital data samples corresponding to the neighborhood to generate optical data, e.g., by subtracting the corresponding neighborhood background level from each of the samples in the neighborhood.

For each of the above methods, the neighborhood background levels can be determined by finding minimum digital data sample values in memory locations corresponding to actual locations adjacent the neighborhood for each optical parameter of each sample in the neighborhood, or by averaging a plurality of digital data sample values in memory outside the neighborhood. Typically, the term "adjacent" means within five scans from the bounds of a neighborhood.

In a further embodiment, time corresponding approximately to the time the digital data was acquired is recorded and stored as synchronous digital time data, whereby each sample has a corresponding digital time point. As used herein, the terms "time corresponding approximately to the time the digital data was acquired" mean the time a given strip of scans is completed. The cell population may also be located on a movable surface, the scanning may proceed in synchrony with a stepping motion of the surface, and the location corresponding to a sample may be derived from digital location data that may be generated, whereby each sample has a corresponding digital time point and location. The movable surface may be a microscope slide, a cuvette into which the cells are inserted, or any other surface upon which or into which cells may be deposited. The cells on the movable surface of all of the above methods and apparatus can be visually observed.

In another embodiment, an additional step of rescanning the population of cells, generating new digital data, location data and time data, and comparing the new data with the corresponding data from a previous scan to determine changes in the cell population may be added.

In a further embodiment of the above methods and apparatus, a cell can be located by detecting a digital data sample corresponding to the edge of the cell first contacted by the beam. In another embodiment, the neighborhood is initially centered around the first edge sample. The method may further include the steps of determining the maximum digital data sample within the neighborhood and then recentering the neighborhood with respect to the maximum sample before estimating a background level for the neighborhood.

The invention also features a method and apparatus for measuring multiple cellular properties including the steps of, and means for, scanning the cell population with a beam to produce sets of digital data samples, different samples representing different locations within the cell population, e.g., storing the digital data in a memory; locating a cell within the population, e.g., by comparing the digital data to a set of preselected thresholds; defining a neighborhood around the located cell; summing all samples of optical data derived from the sets of digital data in a neighborhood to generate optical neighborhood values for the parameters for that neighborhood; comparing each parameter sample in a neighborhood with a set of preselected thresholds to generate a binary neighborhood pattern of samples either above or below the thresholds for each parameter; storing the optical neighborhood values and binary neighborhood patterns in memory; and generating optical properties corresponding to the optical neighborhood values and morphological properties corresponding to the binary neighborhood patterns for each cell.

The optical properties may be generated by applying math functions to one or more of the optical neighborhood values to generate optical property values of the cell corresponding to the neighborhood. The morphological properties may be generated by applying boolean functions to one or more of the binary neighborhood patterns to generate morphological property values of the cell corresponding to the neighborhood.

The term "optical neighborhood value" describes the sum of all optical data in a given neighborhood for one parameter. This optical neighborhood value may then be used as is or processed further to generate optical property values proportional to specific cell constituents corresponding to cells of the population. The term "binary neighborhood pattern" describes a word pattern in memory corresponding to a single neighborhood, i.e., cell, and a specific parameter, that is generated by comparing each sample point in a neighborhood to a threshold and registering a "1" if the point is above a given threshold or a "0" if not. By testing each point, a memory word of ones and zeroes is generated which is the binary neighborhood pattern. This pattern can be further processed to generate morphological property values of the cell.

Each of these methods can include the further steps of estimating a set of background levels for the neighborhood based upon digital data corresponding to locations outside that neighborhood; and subtracting the neighborhood background levels from each of the samples of digital data corresponding to the neighborhood to generate optical data.

The invention also features an apparatus for measuring multiple cellular properties that includes a beam source for generating a beam of electromagnetic radiation, e.g., light, X-rays or infrared radiation that may be controlled by the computer during the scanning process to illuminate the cells with a beam spot comparable in size to the cells to be scanned, an optical signal being generated as a result of the spot illuminating the cells; a surface upon which the cells are located; an optical path for directing the spot from the beam source to the cells on the surface; a scanner that is interposed in the optical path between the light source and the cells for scanning the spot across the surface so that the spot passes over a plurality of cells on the surface; one or more sensors for measuring the optical signals; an analog-to-digital converter arranged to sample the optical signals at a specified rate and to produce digital data; whereby the sampling rate is set such that the distance traveled per time as the spot is scanned between consecutive sampled locations approximates the spot size; data processors for correcting the digital data in the memory, generating optical property values from corrected data points corresponding to multiple constituents of individual cells, and processing the values to determine multiple cellular morphological properties; and a memory for storing the digital data produced by the converters.

In further embodiments, the spot size used in the apparatus and in all of the methods according to the invention is 3 to 50 microns or may be adjusted to be comparable in size to the size of the cells to be scanned. In addition, the wavelength distribution of the beam may be controlled by the data processor.

The scanner of the apparatus according to the invention may be a resonant galvanometer scanner. Furthermore, the surface upon which the cells may be located may be a microscope slide, a cuvette into which the cells are inserted, or any other surface upon which or into which the cells may be deposited.

In another embodiment of the above apparatus and methods, the cell population may be on a movable surface, the scanning may proceed in synchrony with a stepping motion of the surface and digital location data may be generated from which the location corresponding to a sample can be derived.

The digital data produced by the cells and the beam in any of the above methods and apparatus may be derived from sets of analog optical signals. Furthermore, these optical signals may be fluorescence, forward angle light scatter, extinction, or wide angle light scatter.

In another embodiment, the invention also features a method for generating calibrated optical data that characterizes a population of cells in which a number of cells of that population has a constant optical value for a given parameter. This method corrects for beam illumination and light collection differences along each scan line. This method includes the steps of scanning the cell population with a beam along a scan line to produce digital data samples, different samples representing different locations along the scan line within the cell population; storing the digital data; locating a cell within this population; defining a neighborhood around the located cell, the neighborhood containing optical data derived from the stored digital data samples within the neighborhood; determining the location of the maximum digital data sample within the neighborhood and then recentering the neighborhood with respect to the maximum sample; summing all optical data values in a recentered neighborhood to generate an optical neighborhood value for that neighborhood; determining the most frequently occurring optical neighborhood value to define a mode optical value; selecting a subpopulation of cells with optical neighborhood values within a predetermined range around the mode optical value; determining a set of average optical neighborhood values of cells in the subpopulation as a function of cell location along the scan line; computing an array of correction coefficients equal to the ratio of the mode optical value to the average optical value for each location along the scan line to generate an illumination normalization factor; and correcting optical data for each cell at different locations along the scan line by multiplying the optical neighborhood value for that cell by the corresponding illumination normalization factor. The term "mode optical value" describes the optical neighborhood value that occurs most frequently in a complete sample run. The term "illumination normalization factor" describes an array of correction coefficients equal to the ratio of the mode optical value to the average optical neighborhood value of all cells for each location along the scan line.

In another embodiment, the invention also features a method for generating calibrated optical data that characterizes a population of cells. The method includes the steps of scanning a population of calibration particles comprising a known constant parameter with a beam along a scan line to produce digital calibration data samples, different calibration samples representing different locations along the scan line; storing the digital calibration data; locating a calibration particle within the population; defining a neighborhood around the located particle, the neighborhood containing optical calibration data derived from the stored digital calibration data samples within the neighborhood; determining the location of the maximum digital calibration data sample within the neighborhood and then recentering the neighborhood with respect to the maximum digital calibration data sample; summing all optical calibration data values in a recentered neighborhood to generate an optical neighborhood calibration value for that neighborhood; determining the most frequently occurring optical calibration neighborhood value to define a mode optical calibration value; determining a set of average optical calibration neighborhood values as a function of particle location along the scan line; computing an array of correction coefficients equal to the ratio of the mode optical calibration value to the average optical calibration value for each location along the scan line to generate an illumination normalization factor; scanning the cell population with a beam along the scan line to produce digital data samples, different samples representing different locations along the scan line within the cell population; storing the digital data; deriving optical data from the stored digital data; and correcting optical data for each cell at different locations along the scan line by multiplying the optical data for that cell by the corresponding illumination normalization factor.

Other features and advantages of the invention will be apparent from the following description of the preferred embodiments, and from the claims.

DESCRIPTION OF THE PREFERRED EMBODIMENT

The drawings will first briefly be described.

Drawings

MECHANICAL AND OPTICAL SYSTEMS

Figure 1:
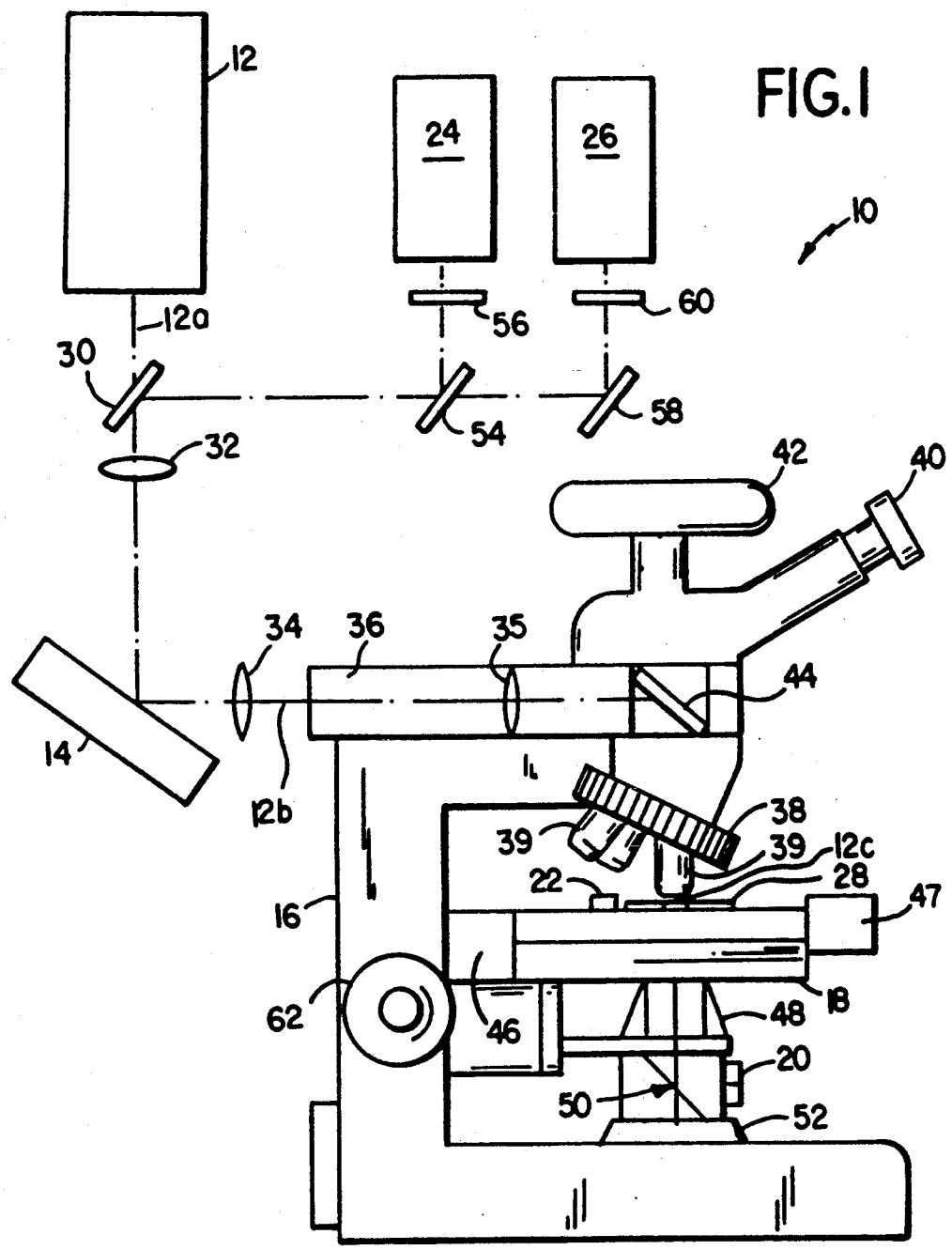
FIG. 1 is a schematic diagram of an instrument for measuring multiple optical properties of biological specimens at high rates of speed.

Referring to FIG. 1, the instrument 10 includes a light source 12, a mirror scanner 14, such as a resonant galvanometer scanner, an epi-illumination microscope 16, a stepper motor controlled stage 18, light detectors 20, 22, 24, 26, and various associated optical components which will be described below. Light source 12 produces a light beam 12a that reflects off of scanner 14 to produce a scan beam 12b and finally illuminates a scan spot 12c of a fixed diameter or size on a specimen plane or surface 28. Specimen plane or surface 28 is positioned on stage 18. Light source 12 is a laser such as, for example, a Helium Neon, Argon ion, Helium Cadmium, or solid state laser, depending on the application. More than one laser may be used for a given application. If this is the case, the beams can be combined using a dichroic mirror so that they are coaxial. For some applications it may be desirable to control the intensity of the laser beams or shutter them under control of a computer. Lasers with multiple wavelength outputs may also be used, in which case, it may be desirable to use a computer-controlled filter, prism or Bragg cell to select a specific wavelength.

After passing through a dichroic mirror 30, the laser beam is imaged by two lenses 32 and 34 onto an epi-illumination field stop 36 of microscope 16. Resonant scanner 14 is located between lenses 32 and 34 and scans the beam across the field stop when electrically driven. The focal lengths of lenses 32 and 34 and the deflection angle of scanner 14, which is proportional to the galvanometer drive voltage, control the size of the spot and the length of the scan at field stop 36 and thus, at specimen surface 28. The scanner is driven at 800 Hz and the spot size at the specimen is 10$\mu$ and the scan length at the specimen is 120$\mu$. These are nominal values and can be changed by the user by rotating microscope nosepiece 38 bearing objectives 39 from the nominal 20X to other higher magnifications to reduce the spot size and scan length or lower magnifications to increase them.

Epi-illumination is used to illuminate the specimen and to transmit fluorescent or scattered light to the viewing eyepiece 40 or to a film or video camera 42. The light transferring assembly 44 may contain a dichroic or partially or fully silvered mirror as well as an optical filter in the viewing path. These assemblies are interchangeable and the microscope used in the described embodiment includes a movable rod to exchange these assemblies.

The specimen surface 28 may be a slide upon which a tissue or cytology specimen is mounted or a cuvette into which a cell specimen is injected. Furthermore, microscope 16 may be an inverted microscope and specimen surface 28 may be a container or dish containing living cells. The optical instrument is designed to accept either a standard or inverted microscope.

The cells of the specimen may be stained to alter their light scattering characteristics or cause them to fluoresce. The scatter or fluorescence of each cell is related either to 1) the amounts of specific cellular constituents such as DNA or proteins or 2) the amounts of one or more fluorescinated antibodies which bind only to specific cell antigens.

The position of the specimen with respect to scanning beam 12b is controlled by X and Y stepping motors 46, 47. These motors are driven in steps that are of a size ranging from a fraction of the spot size to the spot size. This step size is under the control of a computer program. The stage is also provided with sensors to provide signals to the computer to indicate a "Home" or reference position for the stage and to limit its travel. By always moving the stage to Home at the beginning of each run or periodically during a run (i.e., a group of scan strips), it is possible to obtain the absolute position of given cells on the specimen surface so they can be manually reviewed or remeasured. For normal use, the stage can be moved manually by knobs attached to the motors. The stage may also be manually controlled by buttons, a joystick or a computer mouse with a specifically programmed display. The microscope 16 is focused manually by knob 62.

Light scattered from the specimen in the forward direction is primarily related to cell size but may be altered by staining the cell. This scattered light passes through the microscope condenser lens 48, through a dichroic or partially silvered mirror 50, and is imaged onto two sensors 20 that are electrically connected but spaced to allow the incident scan beam image to pass between them. Therefore, only light scattered by the specimen in the forward direction away from the axial light path is collected by sensors 20. The microscope can be used normally to illuminate a specimen by the standard illuminator 52 because the partially silvered or dichroic mirror 50, if suitably chosen, will not significantly reduce illumination. Mirror 50 may be placed into an assembly that mounts directly onto the microscope substage illuminator and is small enough so that it does not interfere with focusing the condenser. The signals from sensors 20 are amplified and become one input for the data acquisition circuit described in more detail below. Although not shown, an additional sensor may be placed behind or below sensors 20 to collect light from the incident scan beam in order to measure extinction.

Light scattered at 90 degrees from the cells is useful for distinguishing certain types of cells such as blood granulocytes, because cells with granules scatter light at oblique angles. Obliquely scattered light will be trapped, with the specimen slide or cuvette acting as a light pipe, and can be detected by a sensor 22 placed at the slide or cuvette edge. This sensor is mounted on the stage in contact with the slide or cuvette and its amplified signal is used as a second input for the data acquisition circuit. Again, this sensor does not interfere with normal microscope usage.

Backscattered or 180 degree scattered light and fluorescent light are collected by objective lens 38 at high numerical aperture and imaged back through the lenses 35, 34, and 32 to dichroic mirror 54 which is designed to reflect the longer wavelength fluorescence if backscatter is not to be measured or to reflect some of the laser source wavelength if backscatter is measured. Dichroic mirror 30 transmits almost all of the laser wavelength. Dichroic mirror 54 splits the light into two parts so as to measure backscatter at the laser wavelength and longer wavelength fluorescence, or two different wavelengths of fluorescence. Mirror 54 can be partially silvered or reflect and transmit light based on polarization if applications require measuring fluorescence depolarization. Mirror 54 reflects part of the incident energy through filter 56 of the appropriate bandpass wavelength onto photomultiplier 24. Similarly, mirror 58 reflects the remaining energy through filter 60 to photomultiplier 26. The signals from the two photomultipliers are amplified and become additional inputs for the data acquisition circuit. Apertures have not been shown in the figures and are used in various places to reduce stray light reflected from the surfaces of the lenses and mirrors.

Electromechanical System

Figure 2:
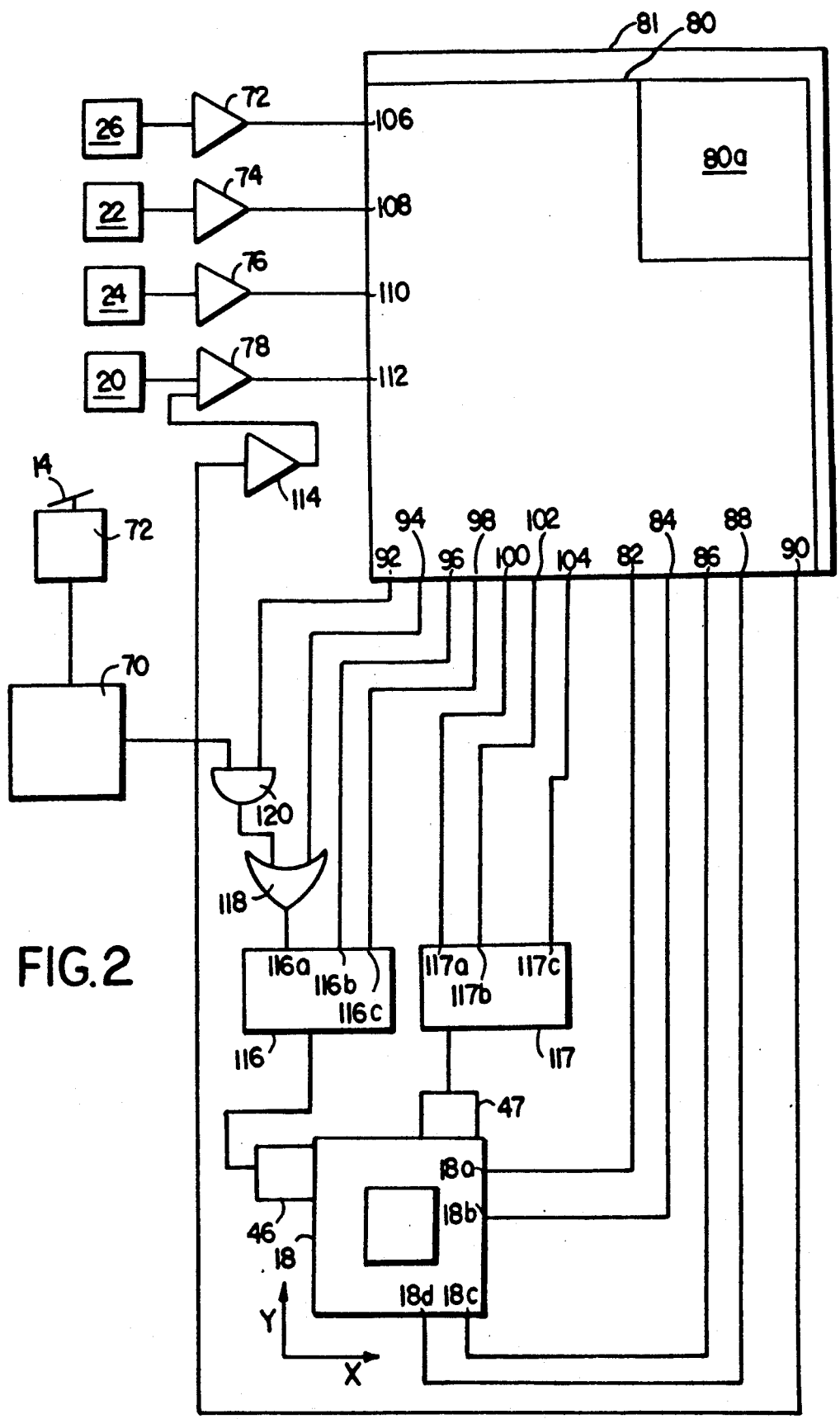
FIG. 2 is a block diagram of the electromechanical circuit used in the instrument shown in FIG. 1.

Referring to FIG. 2, the electromechanical system provides means of inputting signals from the light sensors 20, 22, 24 and 26, the scanner driver 70, and the microscope stage 18, to the computer 81 and outputting signals from the computer to the X stepper motor 46 and Y stepper motor 47 which move the microscope stage 18. This is accomplished by a commercially available circuit board 80 which accepts four analog voltages, digitizes them at rates up to 100,000 Hz with analog-to-digital converter 80a and causes the resultant computer words to be stored in the computer memory under direct memory access (dma) control. Board 80 also accepts digital values from inputs 82-90, which provide limit information from the stage, and provides digital output values on lines 92-104, which control the stage. It also controls the values of two analog voltages used to control the supply voltages to photomultipliers (light detectors) 24 and 26. A detailed description follows.

In one embodiment, circuit board 80 is a Data Translation Model 2828 (Marlborough, N.Y.) which plugs into one of the slots on an 80286 IBM compatible computer. The computer is represented in FIG. 2 by block 81.

Furthermore, photomultipliers 24 and 26 are used to detect fluorescence or backscatter and photosensors 20 and 22 are used to detect forward and oblique scatter emissions from the specimen and are each connected to respective amplifiers 76, 72, 78 and 74. These amplifiers have appropriate gains to provide signal levels of $-10$ to $+10$ volts to circuit board 80 at analog signal inputs 106, 108, 110 and 112. The circuits 72 to 76 are D.C. operational or instrument amplifiers with D.C. "no signal" levels near $-10$ volts. As will be described below, it is necessary to synchronize the position of the scanning mirror 14 with the data acquired by the sensors and converted to a stream of digital data. The digital data stream may be stored as two blocks of 64,000 words each. For synchronization purposes, the D.C. level of circuit 78 is initially set to 0 volts, so that a negative synchronization pulse is easily detected.

Figure 6:
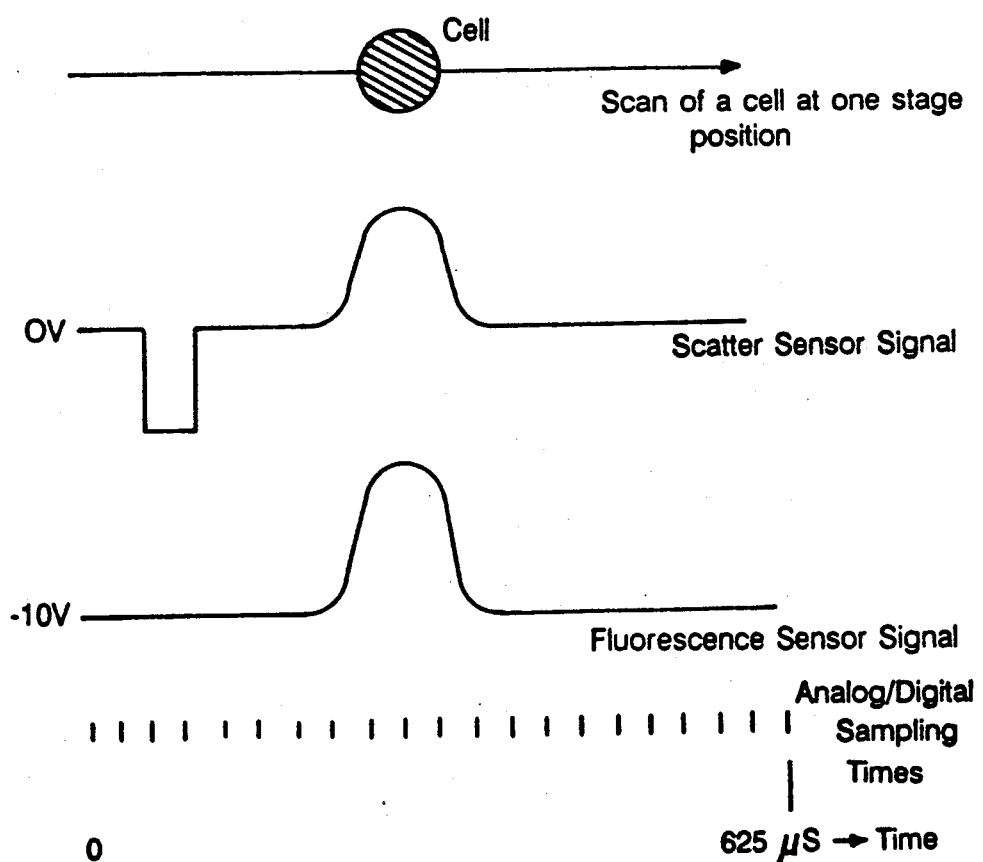
FIG. 6 is a series of graphs representing analog optical data and the corresponding digital data.

Synchronization is accomplished by using a square wave pulse synchronization signal generated by the scanner mirror driver 70 which controls the motion of scan mirror 14 through scanner 72. This signal is modified to a pulse by circuit 114 and, in one embodiment, is added to the sensor signal from sensor 20. Although this reduces the digitization resolution of this sensor input by two, a separate data channel for synchronization is not required. Of course, the synchronization signal may be used as a separate input signal. The signal at input 112 is the forward scatter signal of sensor 20 and the pulse signal is negatively added near one scan extreme (as shown in FIG. 6). As will be seen below, this negative pulse is detected by the program and used to properly synchronize the digital data stored in the computer memory. The sampling rate is set by the user through an initialization program which allows the user to define a Protocol for each test. The Protocol is a monitor screen that the operator uses to set the sampling rate and the various test parameters, area scanned, threshold settings, etc. The number of parameters digitized is also preset and the amplifier gain settings and input/output relationship, i.e., linear or logarithmic, may be used as additional parameters.

The levels of the digital outputs 92, 94, 96, 98, 100, 102 and 104, of circuit board 80 are under the control of the computer program. The digital inputs 82, 84, 86, 88, and 90 are read at specific times also determined by the control of the program. These outputs and inputs are used to control the movement of the microscope stage 18 via X stepper motor 46 and Y stepper motor 47, which are each driven by translator circuits 116 and 117, respectively. The microscope stage is provided with limit switches which indicate when the stage has reached its limit of travel in the x and y directions. These switches generate signals on lines 18a-18d which are used as inputs 82 to 88, respectively, of board 80. Input 90 senses the pulses from scanner 70. Although not shown here, additional digital outputs may be used to control the wavelength of the light source by controlling specific light sources, shutters, or filter positions.

Figure 3:
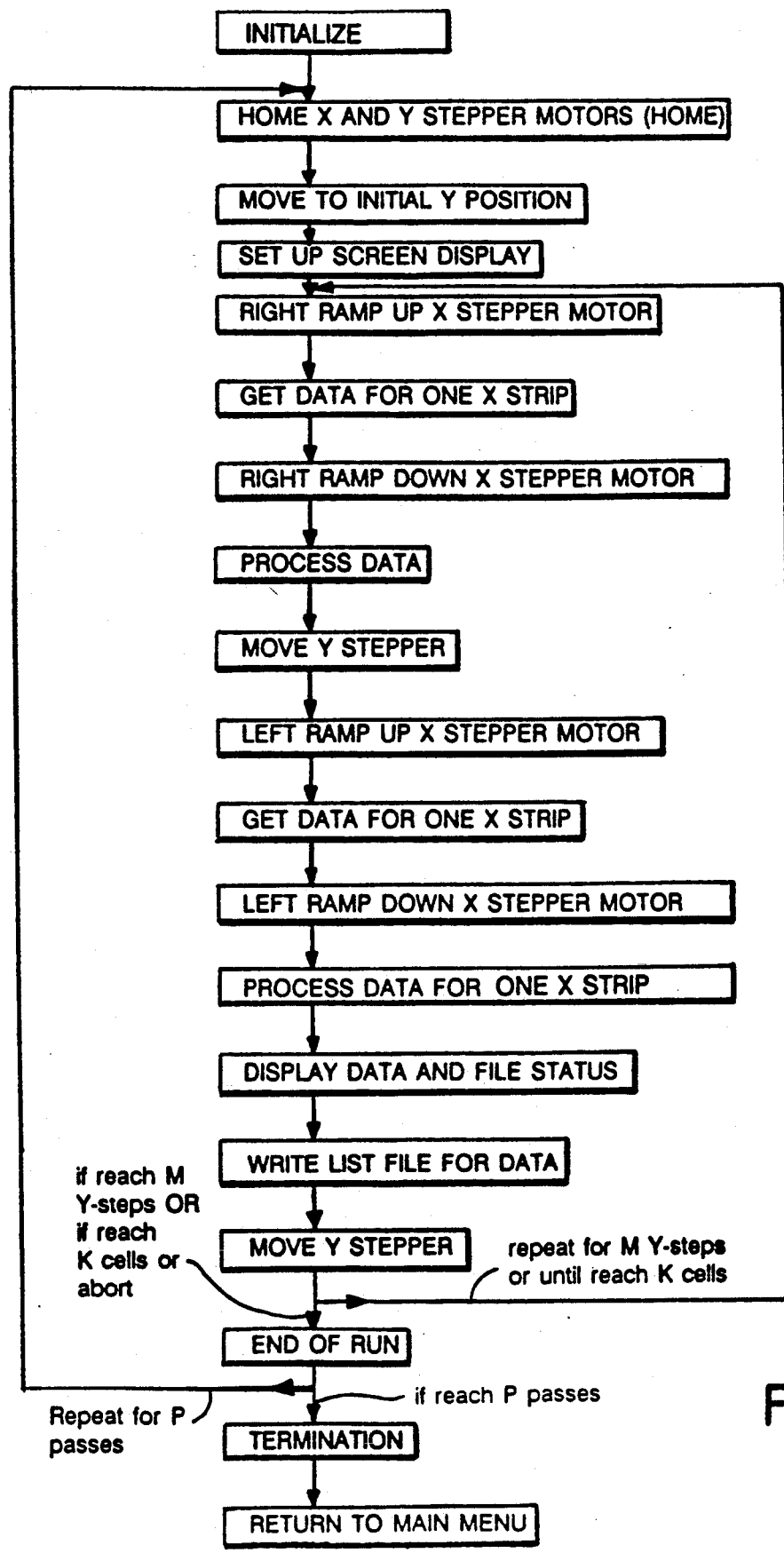
FIG. 3 is a flow chart of the general optical signal data acquisition loop.

The program controlled stage motion is designed to perform the following sequence that is depicted in the flow chart of FIG. 3. First, when the user initiates a test, both stepper motors are moved to a specific "Home" position. This is accomplished by calling a program subroutine to pulse lines 94 and 100 on and off until inputs 82 and 88 indicate that the stage has reached Home. An OR gate 118 passes the signal directly from output 94 to input 116a. Under program control, outputs 96 and 102 are set to produce the proper stage direction by producing signals received at inputs 116b and 117b. As soon as the stage reaches Home, the Y stepper is pulsed to move the stage 18 to the initial y position, then a subroutine is called to move the stage to the right in the x direction by changing the signal on output 96. In one embodiment, the pulse rate on output 94 is ramped-up in rate from about 100 up to 800 pulses per second (pps) for a fixed total number of pulses or distance, typically 100 pulses or steps. This is the ramp-up number. This fixed ramp-up may also be adjusted by the program or by a commercially available ramp-up controller circuit (Metrobyte, Taunton, Mass.).

Figure 4:
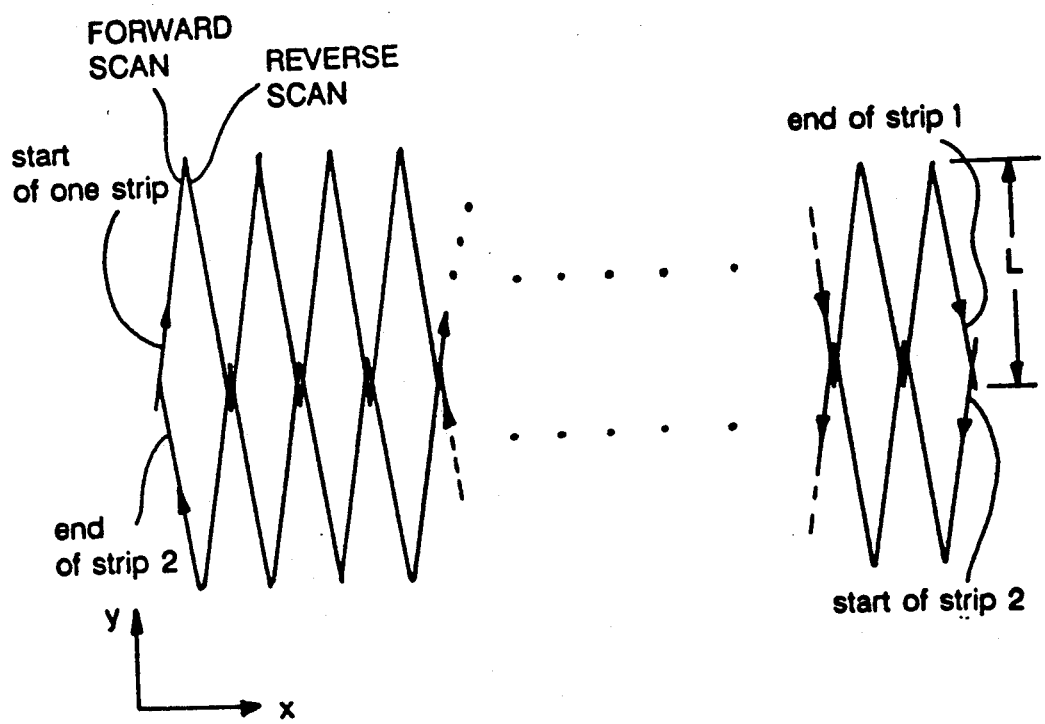
FIG. 4 is a schematic drawing of the scan pattern of the laser beam.

The program produces a rate of 800 pps, which is the scanner frequency, at the end of the ramp-up, so the stepper is moving at full stepping speed at this time. The step size may be either 5 or 10 microns or some other size depending on the level at output 98 which controls the translator 116 through input 116c to produce full or half steps of motor 46. Thereafter, output 92 is programmed to provide an input to AND gate 120 to allow the stepper motor to be directly driven by the synchronization output of mirror scanner driver 70 stepping stage 18 to the right in the x direction at 800 steps per second, e.g., one step for each scan cycle. The stepping motion in conjunction with the scanning motion generated by scanner driver 70 which is perpendicular to the stepping motion creates the scan pattern shown in FIG. 4. In FIG. 4, the scan starts at the left, at the Home position, and forward and reverse scans of length "L" are produced until the end of one scan strip is reached. Such a strip typically encompasses 2500 forward and 2500 reverse scans. An additional circuit may be provided between driver 70 and translator 116 to allow other ratios of scanner rate to stepper rate under control of the user through the Protocol.

An additional parameter of the Protocol is the X scan distance. This distance determines the length of one scan strip. This length can be used to calculate the size required for the data buffers by multiplying the number of parameters measured by the total number of data values digitized per scan strip. The board 80 digitizes inputs, stores them in a buffer, and returns a flag when the buffer is full. At this time, output 92 is set to transfer control of the X stepper from mirror driver 70 to program controlled output 94 via gates 120 and 118. The X stepper is then ramped down in velocity to a stop in a number of pulses or steps equal to the fixed ramp-up number, e.g., 100 steps. The digital data in the two buffers may be processed at the end of a complete scan strip, as will be described below, or it may be processed as it is being digitized. At the conclusion of this scan strip, stepper motor 47 moves the stage in the y direction so that a new scan strip can be run. Output 100 is used to send pulses to input 117a to step the motor; output 102 determines whether movement is in the positive or negative y direction and output 104 determines the size of the steps (5 or 10μ) and passes a signal to input 117c. Again, smaller or larger movements may be used under Protocol control.

After stepping the Y motor 47 to move the specimen "up" or "down" in the y direction a distance equal to 60% of the scan length L, as shown in FIG. 4, the procedure described above, in which the X stepper motor 46 is ramped up in rate and moved the X distance, and ramped back down to a stop is repeated but the stage is moved back to the left in the x direction. The Y stepper then moves the stage in the y direction a number of steps and the complete cycle is repeated. The number M of Y steps are counted by the program and the test is terminated when the Y distance (a given M) is reached as determined by the user through the appropriate Protocol parameter.

System Setup and Calibration

Upon starting the program, the user is asked to select a Protocol either from a set of named Protocols stored on disk memory, which can be modified at that time, or to generate a new Protocol. The Protocol is a set of parameters and demographic information about the tests to be performed on the sample. Demographic information describes the type of sample, the number or name of the sample, and any comments relating to the sample. The Protocol, along with the cell count for the test, is stored with each set of test results to properly identify the data and test conditions. The Protocol parameters are: 1) the four start and end coordinates of the scan area and the X and Y step size, 2) the analog data acquisition rate, 3) the number of sample points processed along each scan line, 4) for each parameter, its name, its gain, a threshold level for cell finding, a morphology threshold used to generate each cell's morphology word (binary neighborhood pattern), a flag to indicate which parameter will be used to find the cell's center, and where its values are displayed on the monitor during the test, 5) the size of the neighborhood (neighborhood is a concept to be described below), 6) the maximum cell count at which the test may be terminated, 7) the number of complete scans and 8) the prefix name of the file in which the test data is stored.

Before beginning any sequence of tests, the user may be required to develop a set of calibration data by methods described in further detail below. The user can select calibration data stored from a previous calibration run or can generate new calibration data. If new calibration data is desired, the user selects a section of the test specimen without cells or uses a specimen with no cells, places it on the microscope stage, and observes that the area to be scanned contains no cells or debris. The output of each parameter over the scan length is displayed continuously as a function of time on the monitor screen during calibration and stage position can be manually controlled. To determine these background values, the user keys the beginning of a background calibration scan and the values of the parameters are digitized at one Y stepper position and one or more X stepper positions for a fixed number of scans on the order of 100. In one embodiment, this is accomplished in that the stage moves only a few steps in the x direction while continuously scanning up and down over generally the same blank (no sample) area. The parameter values of each of the scan sample point positions are averaged over all scans. The average values and their coefficients of variation are displayed on the monitor screen to be checked by the operator to determine whether the machine is operating within the proper range of values. The coefficient of variation is the standard deviation of a measurement divided by the mean of that measurement. These values are stored in memory as an array to be used in calculating cell parameter values if required.

The user can also initiate a second calibration run in which a test specimen provides an optical signal such as fluorescence or scatter. For example, a stained ground surface slide may be used. This is independently scanned as described above to derive a set of normalization factors for one or more parameters for each of the sample points. The calibration slide is scanned twice, the second time with the beam source blocked, so that the normalization factors are equal to the difference in the optical signal with and without the illuminating beam. This eliminates D.C. and other signal noise in the system that is present even in the absence of illumination. If a given parameter is not normalized its factor is one. These normalization factors are used to correct the data values for variations in the optical signal received from the cells due to, e.g., the cell's location on the slide, the variation in the incident laser light, or other variations not related to a cell's constituents. These factors are then multiplied by the data points to remove the effect of these variations from the final measurements.

The normalization factor may also be multiplied by a velocity normalization factor to account for the different velocities along each scan because if most of the scan is utilized, more samples are digitized for cells near the ends of each scan length L because the beam slows, stops and turns in the opposite direction before starting the next scan length L. The velocity calibration factor is the cosine of the distance of a sample point from the center of a scan length and is multiplied by the normalization factor for each sample point and stored as an array to be used later to normalize each sample point value in calculating cell parameter scan values.

In another embodiment, an initial calibration of the device may be avoided by a method of self-calibration that operates during the sample run. This method avoids the need to scan a portion of a test specimen without cells or the use of any special calibration slide. The method generates an illumination normalization factor used to calibrate the optical data to correct for beam illumination and light collection differences along each scan line (length L) across the sample. When the cells of the sample are used to generate the normalization factor, the method is self-calibrating. In the alternative, however, the method can be used with calibration particles in an initial run in which the calibration particles are scanned for a constant optical value of one of a number of known constant parameters, such as size or flurescence, to generate the illumination normalization factor.

This method may be used when the cell population of the sample includes a number of cells that have a constant optical value for some parameter, such as, for example, the DNA value of cells in the resting state or the size of the cells. To achieve an accuracy of about three percent in the calibrated data, approximately one thousand cells of the population having this constant parameter value should be scanned and counted.

For example, in a typical population of cells, a large fraction of those cells are in the resting state ($G_o$) in which all of the cells have the same DNA value. In the ideal population measurement, a substantial number of cells would all have the same value for this particular parameter. Using this ideal as a goal, the optical data is calibrated by the illumination normalization factor to obtain a new set of data with a distribution as close to this ideal result as possible. A normalization factor can be developed and applied to the present sample, to subsequent samples, or, each new sample run can be corrected based on a normalization factor developed from all prior runs.

Figure 9:
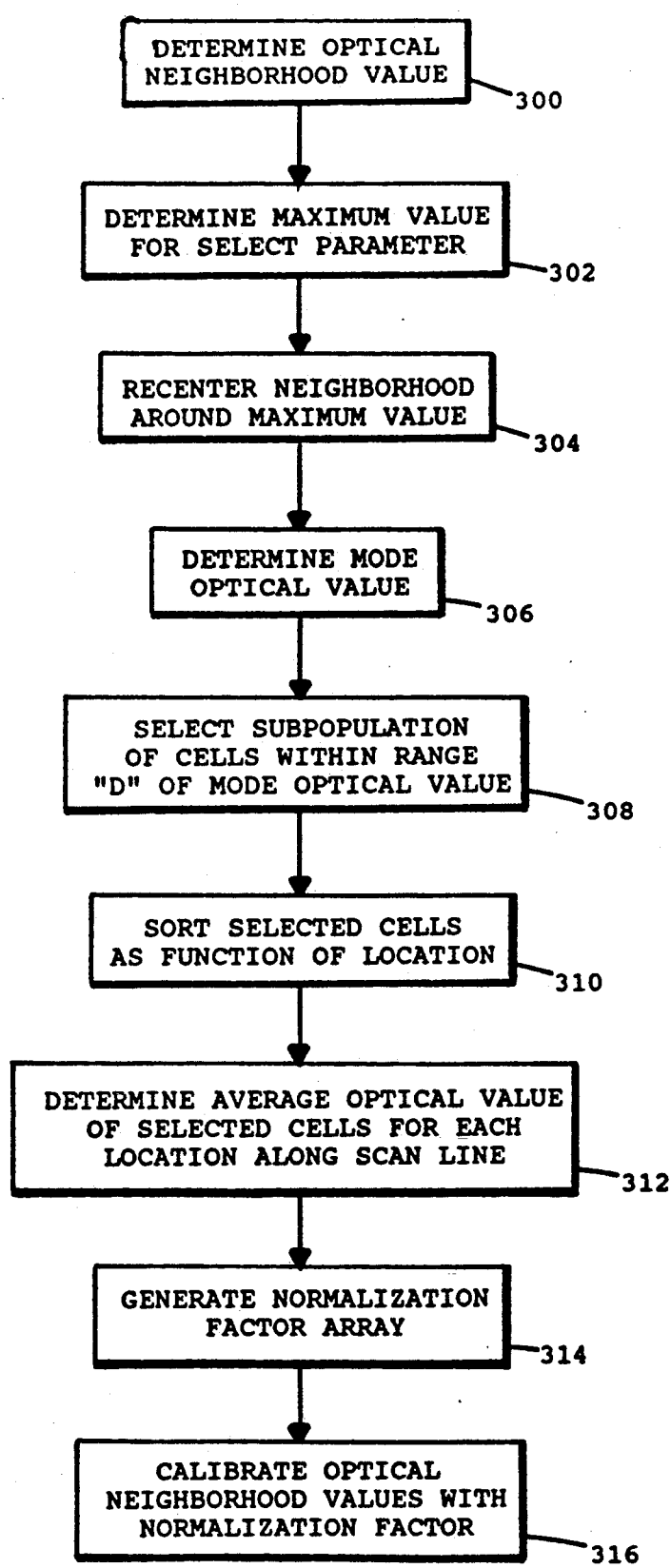
FIG. 9 is a flow chart of the data processing steps of a calibration method.

In particular, this calibration method functions as follows (as illustrated in FIG. 9): As the cells of the sample are scanned, a data list is generated for each cell including, inter alia, the optical neighborhood value (step 300) and the location of the maximum value for a select parameter (step 302), which represents the center of the cell along the scan line, for one or more select parameters. The neighborhood is then recentered with respect to this maximum value (step 304). In this embodiment, the optical neighborhood value is not calibrated for other factors before being multiplied by the illuminization normalization factor. Next, the optical neighborhood value occurring with the highest frequency for the complete sample run is determined and designated as the "mode optical value" (step 306). Next, the optical neighborhood values are reviewed and all cells having optical neighborhood values within a predetermined range of plus or minus "D" of the mode optical value are selected to generate a selected subpopulation of cells (step 308). This subpopulation of cells is then sorted as a function of location, or pixel position, of the maximum value, or center, of each cell along the scan line (step 310). The value of D is user defined and is typically set to between 2 and 6 percent of the mode optical value. If this range is selected to be too broad, it will select cells that do not have the constant value, and if this range is too small, then not enough cells to create an accurate average will be selected. When calibration particles that are known to be uniform are used, there is no need to select a subpopulation of particles within a predetermined range around the mode optical calibration value, because all the particles are the same.

Next, the average optical value of the selected subpopulation of cells for each pixel position along the scan line is determined (step 312). Thereafter, an array of illumination correction coefficients is computed for each scan line including one correction coefficient for each location, or pixel position along a scan line (e.g., for 18 pixels that are preferably used along a scan length L of 30 samples, there would be 18 coefficients) (step 314). Each correction coefficient in the array equals the ratio of the corresponding mode optical value to the average optical value for the associated parameter. This array is the illumination normalization factor.

The array of correction coefficients is one dimensional in that it corrects for variations in light excitation or collection along the scan line. However, the method may also be used to generate such an array for two-dimensional systems. For example, the laser beam may be incrementally moved after each scan over some range in a direction perpendicular to the present scan beam, rather than moving the microscope stage. At the end of this range, the beam movement would be reset to zero and the stage incremented. In this case, the resulting optical data would be corrected as determined by peak location, i.e., the center of the cell in two dimensions.

All summed values, i.e., the optical neighborhood values, for each parameter are then calibrated for differences in illumination along each scan line by finding the peak pixel position for each cell and multiplying the optical neighborhood value by the normalization factor for that scan line position for each parameter (step 316). This generates a calibrated set of optical data.

It is desirable to repeat this process for multiple iterations until the data stabilizes. This is accomplished by using the calibrated optical data generated by the first run as the basis for second and subsequent calibrations. In other words, the calibration method is applied to the initially calibrated optical data stored in the computer memory to generate a new and more accurate illumination normalization factor, which is then multiplied by the initially calibrated optical data to generate a second set of more accurately calibrated optical data. This process can be repeated many times, although the data should stabilize after approximately three iterations. The illumination normalization factor can be applied directly to subsequent sample run optical data or the factor can be updated by applying the method to each run and averaging the latest set of correction coefficients from the coefficients of prior runs and applying the averaged set to the next run.

Optical Signal Data Acquisition

After selecting a Protocol and calibrating the instrument, the operator may initiate one or more data acquisition runs. The purpose of these runs is to scan an area of a test slide defined in the Protocol, find all of the cells on the slide that meet a threshold criteria for a given parameter that is set in the Protocol by the operator, and generate a list for each cell found that contains the corrected optical and morphology values for each parameter of the Protocol, the measurement time, and the X and Y position of each cell with respect to Home. The user places the test specimen on the stage and initiates a run by typing a key on the computer keyboard. The flow chart of FIG. 3 illustrates the general mechanical optical signal data acquisition loop as described above.

The program causes the stage to be driven to Home and then moves the stage over the test area. As the stage moves, the beam is scanned back and forth to create a scan path as shown in FIG. 4. For each X direction scan strip, the optical signal value of each parameter provided by the specimen is digitized by an analog-to-digital (A/D) converter at a sample rate set by the Protocol to create a sequence of digital data sample values. Typically 120,000 such optical signal values are digitized and stored in a buffer memory within 3 seconds. Typically each scan contains 20 samples so that 2000 to 6000 forward and reverse scans corresponding to two to four parameters with steps of 5 to 10 microns cover a length of the same order of magnitude as a slide coverslip. Data acquisition and processing may be done sequentially or simultaneously.

The Relationship Between Spot Size and Sampling Rate

In the described embodiment, the optical system is designed so that the spot size of the scanning laser beam spot $12c$ at the specimen surface 28 is approximately 10 microns when a 20X microscope objective is used in the revolving nosepiece. The spot size can be changed by rotating the nosepiece to 40X to produce a 5 micron spot or to 10X to produce a 20 micron spot.

Figure 5A:
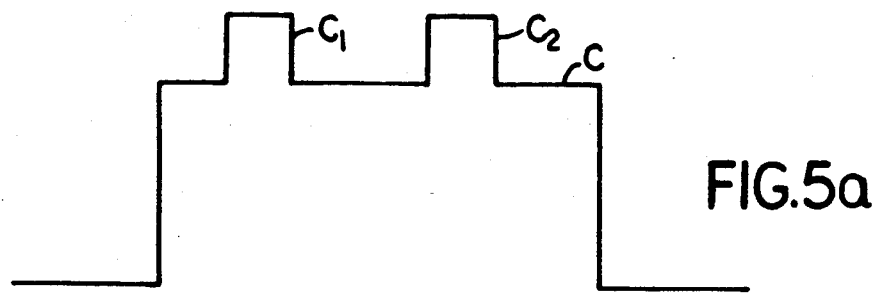
FIGS. 5a to 5d are graphs illustrating the proper sampling rate according to the invention.
Figure 5B:
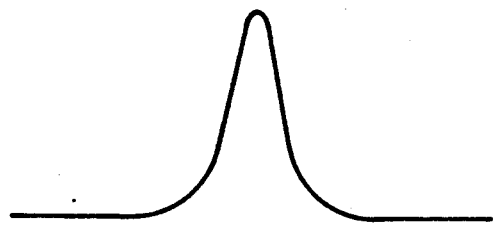
Figure 5C:
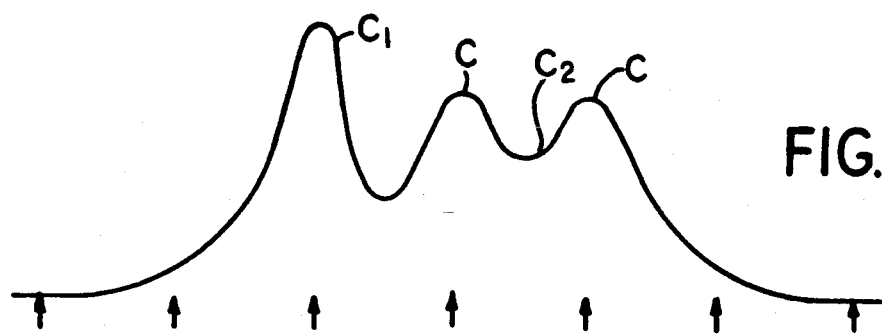
Figure 5D:
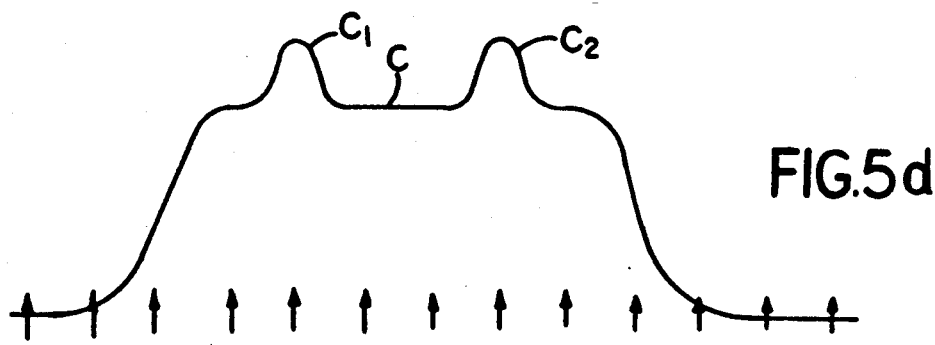

As the beam $12b$ scans across surface 28, a continuous optical analog data stream is produced by each of the instrument's optical sensors 20, 22, 24, 26. FIGS. 5a through 5d show graphically how the analog optical data from a fluorescence sensor is sampled by an A/D converter. FIG. 5a shows a hypothetical profile of a fluorescence signal from a cell with a level C representing a base level of a constituent and with levels representing constituent variations $C_1$ and $C_2$. FIG. 5b shows a scan spot intensity profile. The "size" of the spot is measured at the half-power points of the Gaussian profile. FIG. 5c shows a digital representation of the fluorescence signal with inadequate sampling, and FIG. 5d shows a digital representation of the fluorescence signal with sampling according to the invention. The arrows represent the sampling interval.

The user can define the rate at which each of these continuous optical analog data streams are sampled and converted by the A/D converter and stored as digital data values in the computer memory. The rate can be set using the hardware protocol up to a maximum rate of 100,000 samples per second. A typical experiment uses a rate of 32,000 dual parameter samples per second, i.e., the two analog data streams are each sampled at 31.25 microseconds.

The velocity of scan beam $12b$ is fixed by the resonant frequency of the resonant scanner 70. Such scanners are commercially available with frequencies to 2400 Hz. One embodiment uses an 800 Hz. scanner, i.e., scan beam $12b$ moves forward and back, each with a distance "L", the scan length, 800 times per second, taking 625 microseconds for the beam to move from one end to the other of the scan length L with a cosine velocity profile. (625 $\mu$sec/b 31.25 $\mu$sec=20 the number of sample points per scan length.) The scan path of the laser beam is shown in FIG. 4.

As shown in FIG. 5b the intensity profile of the scan spot $12b$ on the specimen surface 28 is Gaussian. The analog data generated by any sensor from a continuous scan of an optical signal from the specimen is the convolution of the Gaussian intensity profile and the distribution of the desired cellular constituent signal, i.e., the two distributions are multiplied as one is shifted in time.

Consider a case in which a fluorescence dyed cell is scanned. A hypothetical profile of fluorescence is shown in FIG. 5a which represents levels of fluorescence C due to the cell's base level of a constituent and fluorescence due to constituent variations $C_1$ and $C_2$. If the sampling rate is low so that the beam moves more than a spot width between the locations at which the analog data stream is sampled, some of the information in the fluorescence signal will be lost. The digital samples will be added later to try to determine the amount of dye along a line segment. In the case of low sampling, i.e., samples are taken too infrequently, the resultant set of values would not be representative of the convolution of the distributions of the beam intensity profile and the dye distribution because the sampling rate is too low producing "gaps" in the digital data corresponding to the analog data as shown in FIG. 5c. Summing these samples would underrepresent parts of the base level C and furthermore, the information representing the actual increase due to constituent variation $C_2$ is lost between the two peaks representing base level fluorescence C. If the sampling rate is such that successive samples in the specimen plane are spaced apart by the spot size or less, all parts of the specimen will be equally represented as shown in FIG. 5d, because Gaussian profile spots spaced one spot size apart when added produce a uniform distribution along the scan. This is because the Gaussian profiles overlap enough when spaced one "spot size" apart that, when added, the total equals the maximum or peak value of the Gaussian curve. The cell specimen is sampled with close enough spot spacing so that when the samples from a fluorescence sensor are added, with proper calibration, it will yield the accurate amount of the cells' constituents independent of the distribution of that constituent in the cell or the location of the cell on the slide.

The described embodiment uses a conventional circuit card available from Data Translation (DT) for converting analog data to digital values. This card utilizes direct memory access (dma) in which the DT card is set up by the program to continuously sample each of up to four analog signals at a predetermined rate. This DT card also converts each of these analog samples to its digital data value equivalent, and to store each set of signal samples in successive memory locations with a predetermined starting memory location, completing the operation when a predetermined number of memory locations (buffer) is filled with digital values.

The program sets up this analog-to-digital operation by specifying the signals to be sampled, the sampling rate, the initial memory location, and the size of the buffer. One complete X strip is processed from raw data into list data in one batch so that the buffer size must be equal to the number of scans in a strip (typically 2500) times the number of samples in a scan (typically 20) times the number of optical signals used in the experiment (typically 2 to 4); that is, the buffer size is approximately 100,000. When the buffer is full, program control is transferred to the functions that will find cells, find their peak values, and determine their optical and morphological property values. At this point, there is a buffer with typically on the order of 100,000 sequential values in it. The dma operation and list value determination operations can also be overlapped.

Digital Data Processing

Once the digital data sample values are stored in the computer memory (buffer) the data is processed by a variety of protocol controlled functions to correct the data, e.g., for background, to calibrate the data, and to generate the desired optical and morphological property values. These function steps are shown in the flow chart of FIG. 7.

Figure 7:
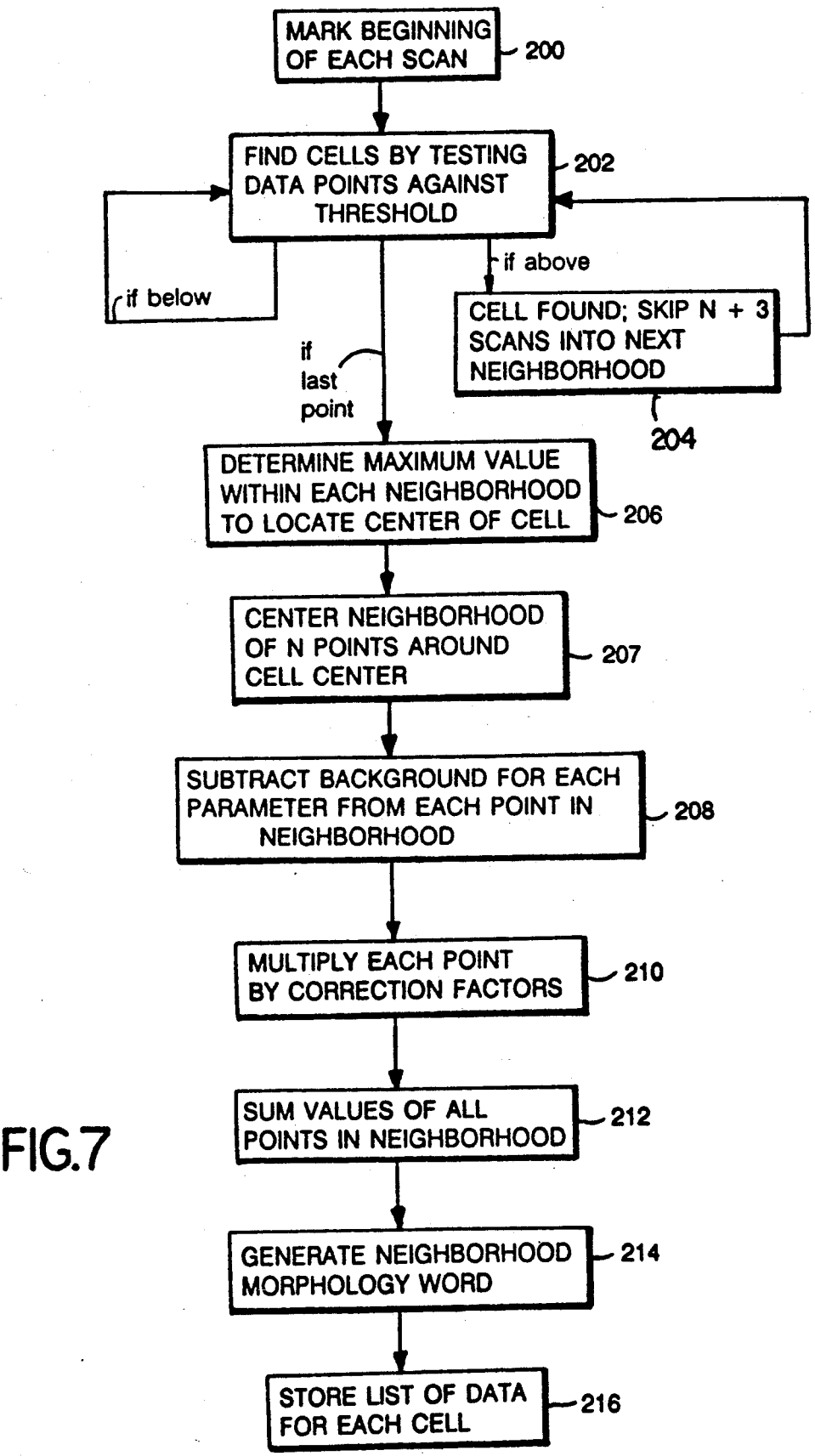
FIG. 7 is a flow chart of the data processing function steps used to manipulate data stored in memory.

The first data processing program function step, 200 in FIG. 7, locates the beginning of each forward scan (typically 2500 per strip) in the strip. As shown in FIG. 6, one of the signals, typically the forward scatter signal, has added to it a synchronization pulse of sufficient amplitude, duration, and negative polarity so that it can be distinguished from all normal signals. The synchronization pulse is derived directly from the mirror scan driver 70, occurring once for each forward scan at the same time for every scan and near its beginning so that this pulse does not interfere with the actual data. In the described embodiment, only the middle (approximately 12) sample points of the 20 sample scan (i.e., there are 20 samples per scan length L) are used and will be referred to as POINTS. A 30 sample scan length would have approximately 18 POINTS. The program first searches successive memory locations of the buffer for sequences of three values that match the shape of the synchronization pulse and produces a table of pointers to all of these locations. The starting location of every data POINT value is fixed at a known displacement in the buffer from each of these pointer locations. Because the relationship of the synchronization signal and scan position is fixed, the start position of every scan can be marked and the data buffer values can each be associated with a specific scan position by appropriate record keeping in the program.

Groups of contiguous points for each parameter are located in memory based upon their distance from the synchronization signals. If parameter samples are taken sequentially, i.e., POINT 1 for parameter A, POINT 1 for parameter B, POINT 2 for parameter A, etc., then these groups of contiguous points will include every other sample in memory (for 2 parameters).

The next function step, 202 in FIG. 7, called by the program is responsible for finding cells. The event of locating an individual cell is called a "cell find". The function causes a search of each of the POINTS of each scan to find values for any parameter (with its background value subtracted) that exceed the Protocol threshold value for that parameter. Thus, any one parameter can be used to find a cell by an increase in that given parameter's signal value caused by that cell.

Background values can be obtained from a calibration area as described above or they can be generated, either by averaging or determining the minimum values, of samples in the same position of scans in one or more prior or subsequent neighborhoods. Initially, the program computes a table of initial background values for the POINTS of a part of a scan strip, i.e., the first approximately 50 scans, to determine the lowest value for all POINTS for each parameter signal. The initial background value for these POINTS is stored in a table.

One of the Protocol parameters of this invention is the size of the neighborhood. The neighborhood has a value N that is typically near five POINTS but is adjusted by the user to the size and concentration of cells in the test. The neighborhood is set to statistically include only one cell.

In the cell find function, a separate step 204 in FIG. 7, defines a neighborhood around each cell found. The neighborhood value N defines the area (POINTS×scans) surrounding the cell find in which other cell finds are prohibited, that is, once a single cell is found in a given neighborhood, the next find must be outside that neighborhood. The number of scans skipped after the end of a neighborhood is typically 3. Also, because data values are added only within the neighborhoods, cell finds are not allowed in areas of the sample at the scan edges which comprise less than a full neighborhood. The present real time, including date, is taken from the computer clock and stored in the cell list. The value of N, which is equal to a number of sample POINTS of a neighborhood and the number of successive scans of a neighborhood is defined in the Protocol. N is preferably odd for ease of defining a center of the neighborhood.

The next function step, 206, compares all values along N POINTS of N forward scans, i.e., within one neighborhood, centered at the location of the cell find to determine the maximum value of that POINT minus its corresponding POINT background value for one of the Protocol determined signal parameters. The maximum value defines the center of the cell and the new location of the cell find. The neighborhood is recentered in step 207. The number of the scan, the POINT number, and the strip number are all stored in the main cell list file to define this new cell location, along with the computer system time.

In the next step, 208, a new set of POINT background values for each neighborhood is computed by determining the minimum values of samples for each parameter signal using a set number of scans (typically 5) that end outside the neighborhood, e.g., just prior to the beginning of the current neighborhood. Subtracting this background from the digital data POINTS generates optical data POINTS in the computer memory.

Illumination intensity, velocity and background as determined by the calibration run and by the program are all taken into account in the next step 210 by multiplying each POINT value for each parameter by an array of POINT illumination correction coefficients and velocity correction coefficients. The next function step, 212 in FIG. 7, sums all corrected optical data values for each parameter for each sample of the defined neighborhood centered at the position of the peak value for that cell. This sum is the optical neighborhood value. In the self-calibration method described above, this optical neighborhood value is not initially calibrated for intensity or velocity, but is corrected in a subsequent step.

In this embodiment, the number of samples of the cell taken in each direction is greater than the projection of cell length in that dimension divided by the spot size in that direction so that when these samples are added, the result accurately represents the integrated value of that cell parameter and can be directly related to the absolute quantity of a given cell constituent. This results from the principle that the samples are taken at a distance apart that is equal to or less than the spot size of the incident light beam. The spot size is selected by choice of microscope objective power, whereas the sampling rate, the step size, and the size of the neighborhood are all selected in the Protocol to adjust the test to the speed, accuracy and sizes of cells tested in the specific test.

The program in the next step, 214, generates a digitized binary neighborhood pattern or morphology word for each cell describing its shape. Each POINT in the neighborhood for each parameter is compared with that parameter's "morphology threshold" set in the Protocol. For each POINT where the value exceeds the morphology threshold, a specific position of the morphology word in memory is set from zero to one and the word is shifted by one. If the threshold is not exceeded, the location is kept at zero and the word is shifted by one. Thus, each parameter of each cell is used to generate a word equal in length to the area of the neighborhood (POINTS × scans) that contains a digital image of the cell. In practice, the size of this word can be made smaller than the number of POINTS to reduce storage space. In a final step, 216, these words are stored in a list for each cell along with data for the neighborhood value generated in step 210, the time of the scan, and cell position data.

Display of Optical and Morphology Parameters

The above set of functions is repeated for each cell find in the buffer representing one X strip. The optical property values (generated from the optical neighborhood value) or the morphological property values (generated from the binary neighborhood pattern) of two parameters are displayed on a monitor screen as a dot whose x position is proportional to one parameter and whose y position is proportional to a second parameter. When a specific number K of cells are found (typically 500) or a specific number of Y-steps (M) is reached, the "run" is completed and a list of values for each cell is written in a file to a fixed disk of the computer. The device also may be programmed to repeat a run, or rescan, for any number P of passes.

To repeat a run, the microscope stage is moved to begin scanning the first X strip and all of the above steps are repeated. Simultaneously, other program functions control the position of the stage. As in the first pass, the stage is initially moved to a HOME position, then to an initial start position and ramped up to scanning speed while keeping track of position, moved in synchronized steps across a strip in the x direction, ramped down in speed to a stop, and stepped in the y direction as described above. In this way, by repeat scanning of the same specimen of cells, the operator can observe kinetic changes in the individual cells.

The list of data generated as described above can be processed by a data display program that can be run at a later time or between strips of the above data acquisition program. The principal features of this program are as follows.

Using a "Data Protocol" the user can define a list of properties that are computed by applying mathematical functions to one or two optical neighborhood values, morphology words or time parameters. For example, an optical property can be an optical neighborhood value for one parameter (e.g., a value that can be converted into a number of picograms of DNA), the ratio of two such values, the time, or the sum of all of the 1 bits of a morphology word, i.e., binary neighborhood pattern (the cell area). These properties are used as the basis for a sequence of cell selections to count and display cell subpopulations on the monitor screen.

Figure 8:
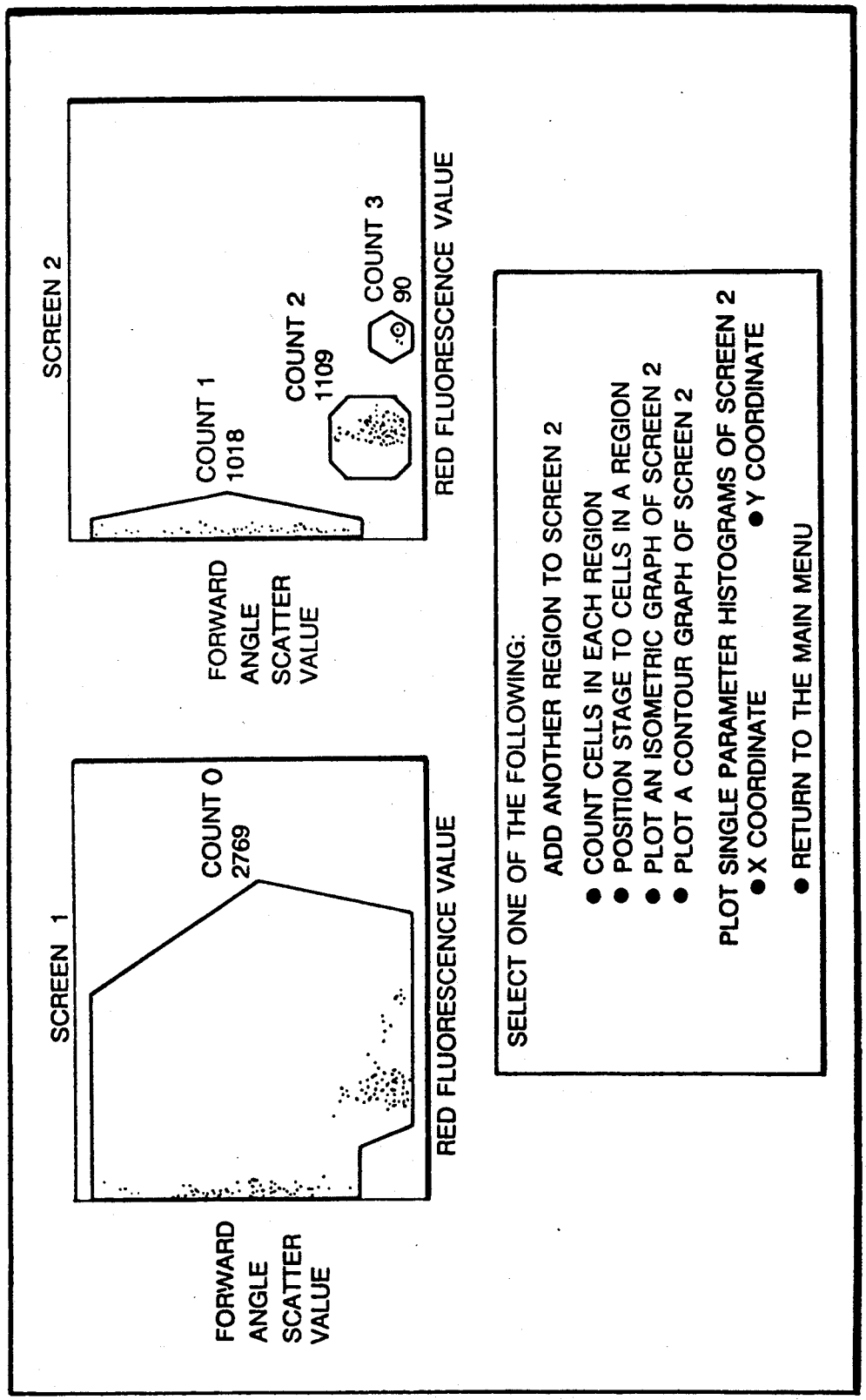
FIG. 8 is a monitor screen display for an actual test run charting red fluorescence value (x-axis) against forward angle scatter value (y-axis).

Screens are generated on the monitor with axes corresponding to each of two selected properties. Each cell is displayed on the screen as a dot whose position on the axis is proportional to a property and whose color is proportional to the number of cells occurring at that screen position. Using a user controlled mouse, for example, a user can bound a selected area (this can be extended to additional areas) of the screen by a polygon. Two additional properties that may be the same or different from those of the first screen are designated in the data protocol. Cells whose properties are within the area of the polygon of the first screen are counted and displayed on a second screen whose coordinates are the second set of properties. A number of polygons, e.g., six, can be drawn on the second screen and cells within each of these regions are counted. As shown in FIG. 8, the counts appear on the screen next to their corresponding regions.

In addition to counting subpopulations of cells based on successive counts of derived properties, the user can display selected data in a variety of other formats including isometric projections or contour maps of any set of properties. Another aspect of the instrument according to the invention, as illustrated in FIG. 8, is the ability of this program to generate a polygon on the monitor screen that represents a specific location or set of parameter values. The program can then instruct the instrument to locate each cell whose properties fall within the polygon area. That is, each polygon contains a subpopulation of cells within the sample that exhibits a specific characteristic common to each of the cells within the polygon. As each cell is automatically positioned under a microscope objective 39 for visual observation, a dot on the screen corresponding to that cell within the population is marked by a blinking circle centered on it (as shown in the lower right hand polygon in FIG. 8).

After completion of each X strip, the values for each cell's parameters are added to a monitor screen display. During each test, the user sees each cell represented as a dot on the screen at a position determined by the values of two parameters or as two such patterns if more than two parameters are used. The axes of these graphs are labeled using the Protocol parameter names. According to the invention, the positions of found cells may also be represented by dots on an additional graph on the screen. After a fixed number of cells is found, typically about 500, the data lists for those cells are stored in a disk file containing a header with the Protocol. After either the total area has been scanned or the Protocol maximum cell count is reached, the remaining cell data is stored in a list file followed by the total cell count.

The user can call for the program to repeat the scan one or more times. In these subsequent passes, all of the above functions, with the optional exception of cell finding, are repeated. The locations of all found cells from the first pass are read into a table in memory and these locations are used at the appropriate times to indicate the starting position of the peak value finding routine. The new time is stored in the new list and all other functions are identical to the first pass.

Data Analysis

The result of the program of the invention is a file containing a set of data for typically 1000 to 100,000 cells. These data values are used as the input to an analysis and display program which can be identical to any of the programs described in the flow cytometry literature. These programs are reviewed in the texts, Melamed, et al. *Flow Cytometry and Sorting* (John Wiley & Sons, 1979, Ch. 20), or Shapiro, H., *Practical Flow Cytometry*, (A. K. Liss, 1985, Ch. 5).

The monitor screen displays of the present invention describing morphology, time and position, however, are another feature of the present invention. For example, time can be represented graphically as one additional parameter along with scatter or fluorescence parameters or specific functions of parameters may be tested against time variable thresholds or displayed as a function of time to implement experiments or tests. Time can also be displayed by modifying dot or contour colors on a display to mark the passage of time. Functions of the morphology word such as the total one bit count indicative of area of that parameter may be used like any parameter. It is contemplated that the large number of total parameters that can be obtained from the morphology and value data can be best analyzed with techniques described in the pattern recognition or artificial intelligence literature to achieve the end goal of identifying specific cell types or pathological cells on a slide.

Once cells with unique parameter values are found by the analysis program, the test specimen can be placed on the microscope stage and a program called to automatically center the stage on each of these unique cells in turn by reading in a list of the X and Y values of cells to be reviewed. Properties of these cells may be displayed on the monitor screen. The user may use this to verify the automatic data analysis, examine the cells to further determine their pathology, check the quality of the manual procedures in a clinical laboratory, or physically separate or sort cells of interest using cookie cutter like devices.

The kinetic behavior of live cells, primarily blood lymphocytes, when reacted with certain antigens during a test, may be an important new method of testing for systemic pathologies such as autoimmune disease or cancer. As described above, cells with specific properties may be identified and their locations stored in memory. The specimen in a cuvette or chamber on the stage can be rescanned and the new values of these selected cells recalculated and listed.

The device according to the invention also contemplates sequential analysis techniques to maximize speed of analysis. Cells of interest found during a first pass will be examined for other parameters or at greater resolutions to determine properties that require greater analysis complexity and time.

Other embodiments are within the following claims.

What is claimed is:

1. A method for generating calibrated cell constituent data that characterizes a population of cells in which a number of the cells has a constant cell constituent value, the method comprising:
   (a) scanning the cell population with a laser beam along a scan line to produce digital data samples, different said samples representing different locations along said scan line within the cell population;
   (b) storing said digital data;
   (c) locating a cell within said population;
   (d) defining, for each cell located, a neighborhood of digital data samples that includes the digital data samples corresponding to said located cell, said neighborhood containing cell constituent data derived from said stored digital data samples within said neighborhood;
   (e) determining the maximum digital data sample within said neighborhood to define the location of said located cell;
   (f) summing all cell constituent data values in said neighborhood to generate a cell constituent neighborhood value;
   (g) processing said cell constituent data representing individual cells to generate an illumination normalization factor to correct cell constituent data for illumination differences as a function of cell location along the scan line; and
   (h) correcting cell constituent data for each cell at different defined locations along the scan line by multiplying the cell constituent neighborhood value for that cell by the corresponding illumination normalization factor.

2. The method of claim 1, wherein said processing of said cell constituent data comprises:
   (a) testing all cell constituent neighborhood values to determine a cell constituent neighborhood value that occurs most frequently to define a mode cell constituent value;
   (b) selecting a subpopulation of cells with cell constituent neighborhood values within a predetermined range around said mode cell constituent value;
   (c) determining a set of average cell constituent neighborhood values of cells in the subpopulation as a function of cell location along the scan line; and
   (d) computing an array of correction coefficients equal to the ratio of the mode cell constituent value to the average cell constituent value for each location along the scan line to generate an illumination normalization factor.

3. The method of claim 2, wherein said predetermined range of cell constituent neighborhood values selecting said subpopulation of cells is from plus or minus 2 to 6 percent of said mode cell constituent value.

4. The method of claim 2, wherein said subpopulation of cells comprises cells in a resting phase ($G_o$).

5. The method of claim 2, wherein said subpopulation of cells is selected to consist essentially of cells of substantially the same size.

6. The method of claim 2, wherein the steps of computing an array of correction coefficients equal to the ratio of the mode cell constituent value to the average cell constituent value for each location along the scan line to generate an illumination normalization factor, and correcting cell constituent data for each cell at different locations along the scan line by multiplying the cell constituent neighborhood value for that cell by the corresponding illumination normalization factor, are repeated iteratively for initially calibrated cell constituent data to compute new illumination normalization factors until said factors are stabilized.

7. The method of claim 6, wherein said computing and correcting steps are each repeated three times.

8. A method for generating calibrated cell constituent data that characterizes a population of cells, the method comprising:
(a) scanning a population of calibration particles comprising a known constant parameter with a laser beam along a scan line to produce digital calibration data samples, different said calibration samples representing different locations along said scan line;
(b) storing said digital calibration data;
(c) locating a calibration particle within said population;
(d) defining, for each particle located, a neighborhood of digital calibration data samples that includes the digital calibration data samples corresponding to said located particle, said neighborhood containing optical calibration data derived from said stored digital calibration data samples within said neighborhood;
(e) determining the location of a maximum digital data calibration sample within said neighborhood to define the location of said located calibration particle;
(f) summing all optical calibration data values in said neighborhood to generate an optical neighborhood calibration value for that neighborhood;
(g) processing said optical calibration data to generate an illumination normalization factor to correct cell constituent data for illumination differences as a function of particle location along the scan line;
(h) scanning the cell population with a laser beam along said scan line to produce digital data samples, different said samples representing different locations along said scan line within the cell population;
(i) storing said digital data;
(j) deriving cell constituent data from said stored digital data; and
(k) correcting cell constituent data for each cell at different defined locations along the scan line by multiplying the cell constituent data for that cell by the corresponding illumination normalization factor.

9. The method of claim 8, wherein said processing of said optical calibration data comprises:
(a) testing all optical neighborhood calibration values to determine an optical calibration neighborhood value that occurs most frequently to define a mode optical calibration value;
(b) determining a set of average optical calibration neighborhood values of particles as a function of particle location along the scan line; and
(c) computing an array of correction coefficients equal to the ratio of the mode optical calibration value to the average optical calibration value for each location along the scan line to generate an illumination normalization factor.

10. The method of claim 9, wherein said population of calibration particles is selected to consist essentially of particles of substantially the same size.

11. The method of claim 9, wherein said population of calibration particles is selected to consist essentially of particles of substantially the same fluorescence.

12. The method of any one of claims 1 or 8, wherein the location of each cell found is recorded and stored.

13. The method of any one of claims 1 or 8, wherein the time corresponding approximately to the time the digital data sample was produced is recorded and stored as synchronous digital time data, whereby each sample has a corresponding digital time point.

* * * * *